Aug. 24, 1937. J. R. BYRUM Plant Pat. 261

AVOCADO

Filed Feb. 20, 1937

Inventor.

J. R. Byrum

By A. Yates Dowell Atty.

Patented Aug. 24, 1937

Plant Pat. 261

UNITED STATES PATENT OFFICE

261

AVOCADO

Joseph R. Byrum, Homestead, Fla., assignor to Redland Avocado Grove, Homestead, Fla.

Application February 20, 1937, Serial No. 126,916

1 Claim. (Cl. 47—62)

My discovery relates to a new and distinct variety of the avocado fruit, having certain desirable characteristics among which may be mentioned the following:

The fruit is unusual in size compared with any other known winter variety of avocado;

The flesh is free from fiber, and of distinctive coloring;

The color and texture of the skin is distinctive and attractive in appearance;

The tree is an unusually vigorous upright grower, well branched with distinctive foliage.

In the drawing, I have attempted to illustrate an avocado fruit characteristic of the present improved variety, and therein:

Figure 1:
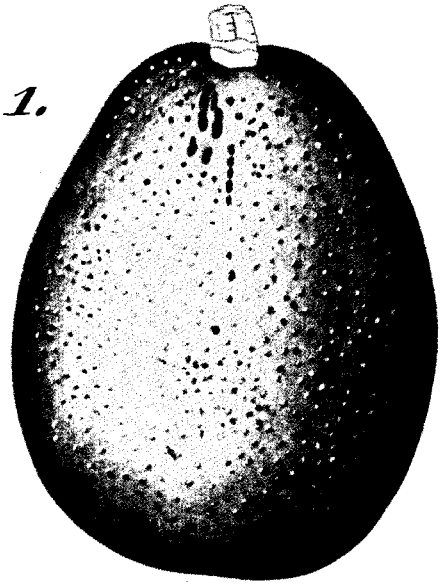
Fig. 1 is a side elevational view in color of the fruit when ripe.
Figure 4:
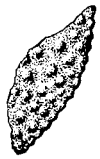
Fig. 4 is a fragment taken from the exterior surface of the avocado, showing in black and white the slightly protuberant formations on the skin of the fruit.
Figure 3:
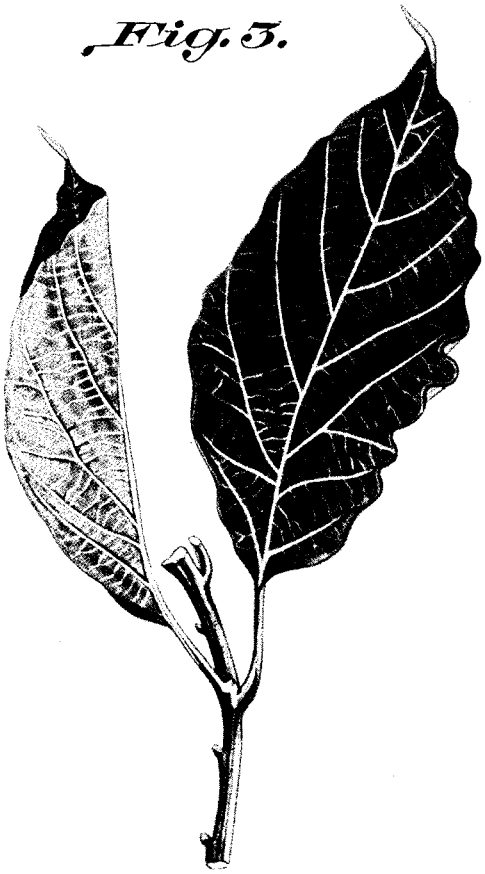
Fig. 3 is a perspective view in color of the leaves with their petioles.
Figure 2:
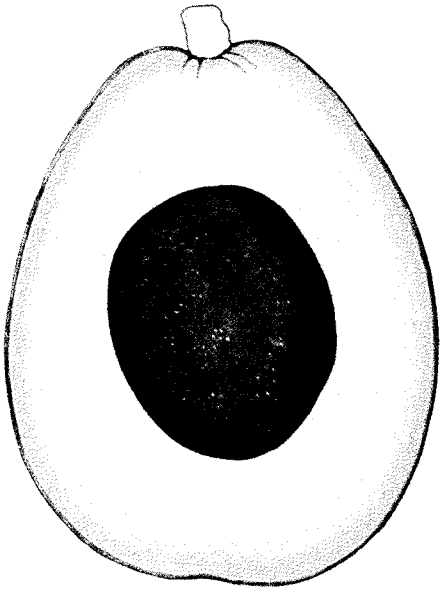
Fig. 2 is a longitudinal section of the fruit of Fig. 1.

The original tree was found as a sapling which grew on a tract of land comprising part of the Redland Avocado Grove, located at Homestead, Florida. The sapling came up under a Waldin tree about two feet from the trunk, and was first discovered in January, 1935, being about three years old at that time. The tract in which the sapling was first discovered comprises about ten acres, and in this tract there were principally Waldins and a few saplings of West Indian race or type; of Guatemalan origin, there were a number of Schmidt variety, one Eagle Rock, also four of Taft variety. The new avocado is therefore probably a cross between the West Indian and Guatemalan types of avocado. Upon the discovery of the original tree or sapling, eighty-seven trees were immediately grafted, being all the graft wood that could then be obtained. More than half were lost in the storms of 1935. In 1936, graft wood was again taken from the parent tree and also from young grafts and additional trees grafted. To date, about seven hundred and thirty-four trees have been grafted, and at the present time, there are about one thousand grafts. Grafting is done during December, January and February. The method of grafting is to saw a tree down, saw across the stump, open stump with a wedge, insert two grafts, remove wedge and cover with grafting wax, tie stiff paper around the stump, and then cover the stump with three inches of sand; getting close to one hundred per cent success.

In 1936, one of the young grafts was overlooked, and the latter is now two years old and has delivered eleven fruits weighing from thirty-two to thirty-six ounces. The tree is one of the most vigorous growing avocados known to me, and is a good heavy producer.

To date the new avocado has been produced only by budding or grafting, and up to the present time the variety has been shielded from inspection by the public and has not been tested elsewhere than on the Redland Acocado Grove near Homestead, Florida.

The parent tree has just been transplanted to where it can be better observed and to prevent it from killing the Waldin.

*Technical description of fruit*

The fruit weighs from twenty-six to thirty-six ounces when mature, varying in size from five and one-half to six inches in length and four to four and one-half inches in width. The skin is dark green in color (about 21L12 of Maerz and Paul) with a glossy speckled surface. The flesh is free from fiber and is of a clear bright yellow color (about 10L2), slightly green (about 19L2) near the skin. The seed is tight and generally round in shape. The oil content runs between 10 and 30%, and the flesh has an excellent nutty flavor.

*Technical description of the tree*

The tree is an unusually vigorous upright grower, and varies from a good to a heavy producer. The fruit matures during the months of December, January and February. The tree is of medium height, well branched and has distinctive foliage (upper side about 15L1—underside about 13H1).

There has been no indication of dwarfing after grafting in comparison with the original tree. Maturing of the fruit occurs at substantially the same time as that of the original tree, the grafting not being followed by an earlier maturity season.

The new avocado tree belongs in the A pollination group; it is decidedly resistant to scab, and in fact it has been found of a hardier and more robust growth than other known prior varieties of this general type.

The variety to date has not been characterized or described in print.

I claim:

The winter variety of avocado substantially as herein disclosed, characterized by the tree's vigorous growth, fruit's size, texture and color, and the distinctive foliage.

JOSEPH R. BYRUM.